United States Patent
Rivera et al.

(10) Patent No.: US 9,493,400 B2
(45) Date of Patent: Nov. 15, 2016

(54) PROCESS FOR PREPARING FLUOROLEUCINE ALKYL ESTERS

(71) Applicant: Merck Sharp & Dohme Corp., Rahway, NJ (US)

(72) Inventors: Nelo Rivera, Milford, NJ (US); Yadagiri R. Pendri, Storrs, CT (US); Sreenivas Mende, Hyderabad (IN); Bramhananda N. Reddy, Hyderabad (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 39 days.

(21) Appl. No.: 14/387,945

(22) PCT Filed: Mar. 25, 2013

(86) PCT No.: PCT/US2013/033666
§ 371 (c)(1),
(2) Date: Sep. 25, 2014

(87) PCT Pub. No.: WO2013/148554
PCT Pub. Date: Oct. 3, 2013

(65) Prior Publication Data
US 2015/0045575 A1    Feb. 12, 2015

Related U.S. Application Data

(60) Provisional application No. 61/617,878, filed on Mar. 30, 2012.

(51) Int. Cl.
| | |
|---|---|
| *C07B 57/00* | (2006.01) |
| *C07C 227/16* | (2006.01) |
| *C07C 227/18* | (2006.01) |
| *C07C 227/34* | (2006.01) |
| *C07C 229/08* | (2006.01) |
| *C07C 229/20* | (2006.01) |
| *C07C 249/02* | (2006.01) |
| *C07C 309/19* | (2006.01) |

(52) U.S. Cl.
CPC ............ *C07C 227/16* (2013.01); *C07B 57/00* (2013.01); *C07C 227/18* (2013.01); *C07C 227/34* (2013.01); *C07C 229/08* (2013.01); *C07C 229/20* (2013.01); *C07C 249/02* (2013.01); *C07C 309/19* (2013.01); *C07B 2200/07* (2013.01); *C07C 2102/42* (2013.01)

(58) Field of Classification Search
CPC . C07B 57/00; C07B 2200/07; C07C 227/16; C07C 227/18; C07C 227/34; C07C 229/08; C07C 229/20; C07C 249/02; C07C 309/19; C07C 2102/42
See application file for complete search history.

(56) References Cited

U.S. PATENT DOCUMENTS

| | | | |
|---|---|---|---|
| 3,221,046 A | | 11/1965 | Johnson et al. |
| 3,976,680 A | * | 8/1976 | Clark ........................... 546/335 |
| 4,656,303 A | * | 4/1987 | Kurono ................... C07B 57/00 558/354 |
| 5,714,471 A | | 2/1998 | Rowe et al. |
| 7,429,674 B2 | | 9/2008 | Devine et al. |
| 7,468,365 B2 | | 12/2008 | Audia et al. |
| 2007/0059812 A1 | | 3/2007 | Truppo et al. |

OTHER PUBLICATIONS

Woo et al., "Diastereoselective isothiourea iodocyclization for manzacidin synthesis," Tetrahedron Letters, 44 (2003) 2881-2883.*
International Search Report and Written Opinion for PCT/US13/33666 mailed Jun. 28, 2013, 9 pages.
Limanto, J. et al, An Efficient Chemoenzymatic Approach to (S)-ç-Fluoroleucine Ethyl Ester, J. Org. Chem., 2005, 2372-2375, 70.
March, Jerry, Advanced Organic Chemistry, New York, John Wiley and Sons,1985, ISBN 0-471-88841-9, pp. 385; 679-680.
Nadeau, C. et al., A Concise Synthesis of (S)-g-Fluoroleucine Ethyl Ester, Synlett, 2006, 291-295, 2.
Drouin, C. et al., Total synthesis of (.+−.)-manzacidin D, Tetrahedron Letters, 2004, 7197-7199, 45(39).
Supplemental European Search Report for 13769309.9 mailed Oct. 21, 2015, 6 pages.

* cited by examiner

*Primary Examiner* — Paul A Zucker
*Assistant Examiner* — Mark Luderer
(74) *Attorney, Agent, or Firm* — Nicole M. Beeler; Catherine D. Fitch

(57) ABSTRACT

This invention relates to a resolution process for the preparation of fluoroleucine alkyl esters.

10 Claims, No Drawings

PROCESS FOR PREPARING FLUOROLEUCINE ALKYL ESTERS

CROSS REFERENCE TO RELATED APPLICATIONS

This application is a U.S. National Phase application under 35 U.S.C. §371 of PCT Application No. PCT/US13/033666 filed Mar. 25, 2013, which claims priority from U.S. Provisional application Ser. No. 61/617,878, filed Mar. 30, 2012.

BACKGROUND OF THE INVENTION

γ-Fluoroleucine-α-amino acids, alkyl esters and their derived peptides have been widely employed as potential pharmaceutical agents due to their broad biological properties, which include enzyme inhibitors, receptor antagonists and lipophilicity enhancing agents. While much development has focused on preparation of various fluorinated analogues of natural and non-proteinogenic amino acids, asymmetric synthesis of γ-fluoro-α-amino acids still remains a challenge. In this regard, stereoselective incorporations of the γ-F-containing side chain have been mostly executed by either chiral auxiliary-directed diastereoselective alkylation, chiral phase transfer-catalyzed alkylation of protected amino acid precursors or enzymatic hydrolysis of suitable precursors.

The instant invention describes novel resolution based preparations of fluoroleucine alkyl esters which comprise efficient throughput processes.

SUMMARY OF THE INVENTION

By this invention, there are provided processes for the preparation of compounds of structural formula I:

I.

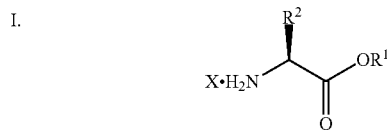

comprising the steps of:
a. alkylating an imine carboxylate of formula II with an alkylallyl halide to form a substituted imine of formula III;

II.

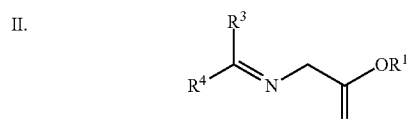

III.

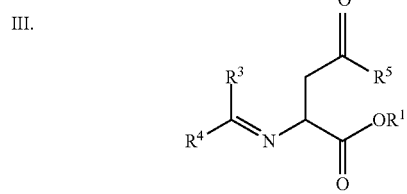

b. deprotecting the substituted imine of formula III with an acid to yield an amine of formula IV;

IV.

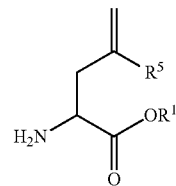

c. resolving the amine of formula IV with a chiral protic acid:
d. fluorinating the resolved amine to yield the compound of formula I wherein $R^1$ is $C_{1-5}$ alkyl;
$R^2$ is $C_{1-5}$ fluoroalkyl;
$R^3$ is aryl or heteroaryl;
$R^4$ is aryl or heteroaryl;
$R^5$ is $C_{1-3}$ alkyl;
X is $H_2SO_4$, L-tartaric acid, D-BOC proline, L-(−)-10-camphorsulfonic acid or N-acetyl-D-phenyl alanine

DETAILED DESCRIPTION OF THE INVENTION

By this invention, there are provided processes for the preparation of compounds of structural formula I:

I.

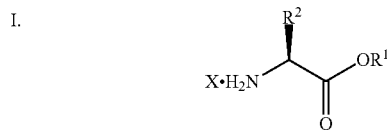

comprising the steps of:
a. alkylating an imine carboxylate of formula II with an alkylallyl halide to form a substituted imine of formula III;

II.

III.

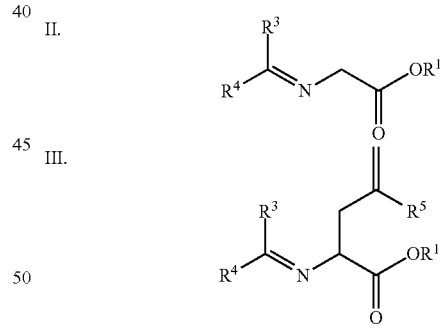

b. deprotecting the substituted imine of formula III with an acid to yield an amine of formula IV;

IV.

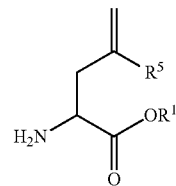

c. resolving the amine of formula IV with a chiral protic acid;

d. fluorinating the resolved amine to yield the compound of formula I wherein $R^1$ is $C_{1-5}$ alkyl;

$R^2$ is $C_{1-5}$ fluoroalkyl;

$R^3$ is aryl or heteroaryl;

$R^4$ is aryl or heteroaryl;

$R^5$ is $C_{1-3}$ alkyl;

X is $H_2SO_4$, L-tartaric acid, D-BOC proline, L-(−)-10-camphorsulfonic acid or N-acetyl-D-phenyl alanine In an embodiment of the invention, $R^1$ is ethyl.

In an embodiment of the invention, $R^3$ is aryl. In a class of the invention, $R^3$ is phenyl.

In an embodiment of the invention, $R^4$ is aryl. In a class of the invention, $R^4$ is phenyl.

In an embodiment of the invention, $R^5$ is methyl.

In an embodiment of the invention, X is $H_2SO_4$. In another embodiment of the invention, X is L-tartaric acid. In another embodiment of the invention, X is D-BOC proline. In another embodiment of the invention, X is L-(−)-10-camphorsulfonic acid. In another embodiment of the invention, X is N-acetyl-D-phenyl alanine.

In an embodiment of the invention, there are provided processes for the preparation of compounds of structural formula IA:

IA.

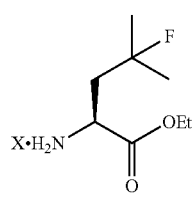

comprising the steps of:

a. alkylating an imine carboxylate of formula IIA with methallyl halide to form a substituted imine of formula IIIA;

IIA.

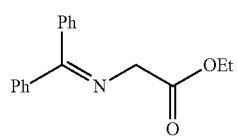

IIIA.

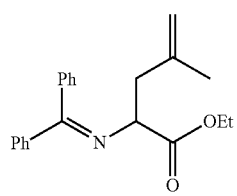

b. deprotecting the substituted imine of formula IIIA with an acid to yield an amine of formula IVA;

IVA.

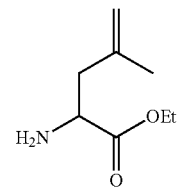

c. resolving the amine of formula IVA with a chiral protic acid, optionally in the presence of an aromatic aldehyde;

d. fluorinating the resolved amine to yield the compound of formula IA; wherein X is $H_2SO_4$, L-tartaric acid, D-BOC proline, L-(−)-10-camphorsulfonic acid or N-acetyl-D-phenyl alanine. In an embodiment of the invention, X is $H_2SO_4$. In another embodiment of the invention, X is L-tartaric acid. In another embodiment of the invention, X is D-BOC proline. In another embodiment of the invention, X is L-(−)-10-camphorsulfonic acid. In another embodiment of the invention, X is N-acetyl-D-phenyl alanine.

An imine carboxylate of formula II is combined with an alkylallyl halide to form a substituted imine of formula III. In an embodiment of the invention, the imine carboxylate and the alkylallyl halide are combined in the presence of a strong base and a polar aprotic solvent. In one aspect of the invention, the strong base has a pKa of greater than 20. In one class of the invention, the strong base is potassium t-butoxide, lithium t-butoxide, sodium t-butoxide, lithium diisopropylmaide (LDA), sodium hydride, n-BuLi, sec-BuLi, t-BuLi, Lithium bis(trimethylsilyl)amide (LiHMDS), Sodium bis(trimethylsilyl)amide (NaHMDS), Potassium bis(trimethylsilyl)amide (KHMDS), Lithium tetramethylpiperidide (LiTMP) or a mixture thereof. In a subclass of the invention, the strong base is potassium t-butoxide. In one class of the invention the polar aprotic solvent is dimethylformamide (DMF), dimethylacetamide (DMAC), N-methylpyrrolidone (NMP), 1,3-Dimethyl-3,4,5,6-tetrahydro-2(1H)-pyrimidinone (DMPU) or a mixture thereof. In one class of the invention, this combination is performed at a temperature of about −15° C. to about 20° C. In a subclass of the invention, the temperature is −5° C. to 5° C.

The substituted imine of formula III is deprotected with an acid to yield an amine of formula IV. In a class of the invention, the acid has a pKa of less than or equal to 1. In a subclass of the invention, the acid is hydrochloric acid, triflic acid, sulfuric acid, p-toluenesulfonic acid, naphthalene disulfonic acid, trifluoroacetic acid (TFA) or a mixture thereof. In a subclass of the invention, the acid is hydrochloric acid.

The amine of formula IV is resolved with a chiral protic acid forming an acid-amine salt. In a class of the invention, the chrial protic acid is D-(+)-camphor-10-sulfonic acid, D-BOC-proline, di-p-tolyl-D-tartaric acid, N-acetyl-D-phenyl alanine or mixtures thereof. In a subclass of the invention the chrial protic acid is D-(+)-camphor-10-sulfonic acid.

The instant invention also comprises a process for chemical dynamic-kinetic resolution using an aromatic aldehyde and D-(+)-camphor-10-sulfonic acid to provide the CSA salt more efficiently by racemization of the undesired enantiomer of IV in-situ.:

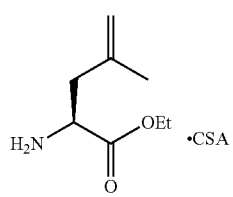

Suitable aromatic aldehydes include, but are not limited to, dichlorobenzaldehyde, benzaldehyde, salicylaldehyde, 5-nitrosalicylaldehyde, 3-carboxybezaldehyde, 4-carboxybenzaldehyde, 3-nitro-5-bromobenzaldehyde, 3,5-dinitrobenzaldehyde, picolinaldydehyde and pyridoxyl-5-phosphate. In a class of the invention, the aromatic aldehyde is 5-nitrosalicylaldehyde.

After resolution, the amine salt is fluorinated. Many fluorinating agents can be used in the present invention. In one class of the invention, the fluorinating agent is Olah's reagent (HF in the form of Pyridine·9HF), HF-pyridine, HF-triethylamine, HF-Urea, HF-melamine, HF or mixtures thereof. In a subclass of the invention, the fluorinating agent is Olah's reagent. The fluorinated amine is then treated with sulfuric acid to yield a compound of formula I.

The term "alkyl" as used herein shall mean a substituting univalent group derived by conceptual removal of one hydrogen atom from a straight or branched-chain acyclic saturated hydrocarbon (i.e., —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, etc).

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C═O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The present invention also includes compounds of structural formula IA:

IA.

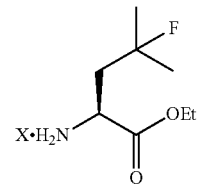

Wherein X is H$_2$SO$_4$, L-tartaric acid, D-BOC proline, D-(+)-10-camphorsulfonic acid or N-acetyl-D-phenyl alanine.

The present invention also includes alkene-amine L-(−)-10-camphorsulfonic acid salts of the following formula:

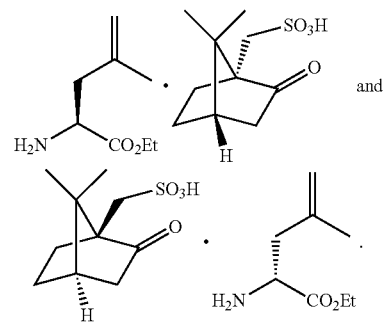

In the examples below, various reagent symbols and abbreviations have the following meanings:
HCl: Hydrochloric acid
HF: Hydrogen fluoride
H2SO4: Sulfuric acid
KOtBu: Potassium t-butoxide
MTBE: t-Butyl methyl ether
DMF: Dimethylformamide
(+)-CSA: D-(+)-camphor-10-sulfonic acid
DBDMH: N,N'-dibromodimethylhydantoin
Ee: Enantiomeric excess The following examples further illustrate the processes of the instant invention and details for the preparation of the compounds of the present invention. Those skilled in the art will readily understand that known variations of the conditions and processes of the following preparative procedures can be used to prepare these compounds. All temperatures are degrees Celsius unless otherwise noted.

EXAMPLE 1

Preparation of ethyl 2-[(diphenylmethylene)amino)-4-methylpent-4-enoate

Ethyl N-(diphenylmethylene)glycinate (150 g, 0.56 mol) and DMF (600 mL) at room temperature under nitrogen atmosphere into a reactor and cooled to −5° C. Sodium tert-butoxide (55.0 g, 0.57 mol) was slowly added in portion-wise keeping the temperature below 5° C. After completion of addition, the reaction mixture was stirred for 30 min at the same temperature. Methallyl chloride (45 g, 0.53 mol) was added slowly at 0° C. and stirred for 20 min at the same temperature. After completion of the reaction, it was poured into ice water (6 L) keeping the temperature below 0° C. and stirred for 1 h at room temperature. Product precipitated out of water. The solid product was filtered and washed with water (100 mL) and the wet cake was dried under vacuum at room temperature to obtain ethyl 2-[(diphenylmethylene)amino)-4-methylpent-4-enoate in 91% yield.

EXAMPLE 2

Preparation of ethyl 2-amino-4-methylpent-4-enoate (D)-(+)-CSA Salt

A solution of alkylated product 2 (65.0 g) in MTBE (185 mL) was cooled to 5° C. and treated with 1N HCl (325 mL). The resulting acidic solution was stirred for 3 h at room temperature. The aqueous layer was separated and washed with MTBE (145 mL×2). The aqueous layer was basified to pH 9.5 with 30% aqueous ammonium hydroxide solution and extracted with MTBE (3×125 mL). The combined organic layer was washed with water (50 mL) and brine (50 mL). The organic layer was concentrated to afford the product 3 (24.1 g) as pale yellow oil in 76% yield. A solution of olefin 3 (22.7 g) in MTBE (45 mL) was treated with (D)-(+)-camphorsulfonic acid (34.75 g). The suspension containing the CSA salt 4 was stirred for 1 h at room temperature. The CSA salt 4 was filtered and washed with MTBE (25 mL). The cake was dried under vacuum to obtain white crystalline CSA salt 4 (22.7 g) in ~38% yield with ~96.5-98.5% ee.

EXAMPLE 3

Preparation of ethyl 2-amino-4-methylpent-4-enoate (D)-(+)-CSA Salt Via DKR Process Ethyl 2-amino-4-methylpent-4-enoate (81.0 g, 0.52 mmol) in MTBE (250 mL) was charged into a round bottomed flask at room temperature. To this solution, (D)-(+)-camphorsulfonic acid (101.25 g, 0.44 mmol) was added in portion-wise. The suspension became a clear solution and the temperature of the solution rises to ~60 ° C. slowly in about 15 minutes. The solution is allowed to slowly cool to room temperature. To this solution, 5-nitrosalicylaldehyde (1.8 g, 0.0108 mmol) was added and the resulting yellow solution was stirred at room temperature for 12 h. The solid CSA salt was filtered and washed with MTBE (250 mL). The cake was dried under vacuum to obtain white crystalline CSA salt in ~75% yield (150.0 g) with >97.5% chiral purity.

EXAMPLE 4

Preparation of (S)-fluoroleucine Sulfate Salt

70% HF-urea (229.7 g, 2.32 mmol) was charged into a HDPE flask at room temperature and then cooled to −10° C. to −15° C. under nitrogen. (S)-Ethyl 2-amino-4-methylpent-4-enoate, (+)-camphorsulfonic acid salt (150.0 g, 0.39 mmol) was added portion-wise keeping the temperature below 0° C. Slowly warmed the reaction mixture to room temperature and continued the stirring for ~3 h at room temperature. After completion of the reaction, the mixture was cooled to −15° C. and added to -10 ° C. solution of 30% aqueous ammonia solution keeping the temperature below −10 ° C. The precipitated CSA salts were filtered and discarded. The basic aqueous filtrate was extracted with MTBE (3×50 mL). The combined MTBE layer was washed with water (50 mL) followed by brine (50 mL). The organic layer was assayed and taken directly for purification with DBDMH.

The above obtained crude fluoroleucine in MTBE was charged into a round bottomed flask. Water (10 mL) was added and cooled to 0-5° C. 1,3-Dibromo-5,5-dimethylhydantoin (DBDMH; 33.13 g; 0.116 mmol) was slowly added keeping the temperature below 0° C. Trifluoroacetic acid (60 mL) was slowly added keeping the temperature below 0° C. Warmed the reaction mixture to RT and stirred for 4 hour. The aqueous layer was separated and extracted the organic layer with 1N aqueous HCl (3×25 mL). The combined aqueous layer was carefully pH adjusted to 9.0 to 9.5 with aqueous ammonium hydroxide. The aqueous layer was extracted with MTBE (3×50 mL) and the combined organic layer washed with brine and dried over 3A molecular sieves (50 g). The MTBE layer was assayed for (S)-fluoroleucine based on HPLC assay (64.0 g, 60% overall yield from (S)-Ethyl 2-amino-4-methylpent-4-enoate-CSA salt.

The MTBE layer containing the Fluoroleucine free base (10.3 g, 58.2 mmol) was charged into a glass lined reactor and cooled to 0-5° C. Concentrated sulfuric acid (5.35 g, 54.3 mmol) was slowly added while stirring. After stirring for 3 hours at room temperature the solid was filtered. The wet cake was dissolved in acetonitrile (10 mL) and warmed to 40° C. MTBE (30 mL) was added, the slurry stirred for 3 hours at room temperature and the solid was filtered and dried under vacuum at room temperature to afford the white crystalline sulfate salt in ~52% overall yield.

EXAMPLE 5

Preparation of (S)-fluoroleucine L-tartrate Salt

A suspension of L-tartaric acid (84.7 g, 0.56 mol) and ethanol (300 mL) was heated at 60° C. for 30 min and to the resulting clear solution was added (S)-fluoroleucine in MTBE (100 g, 0.56 mol in 300 mL) over 30 minutes. After stirring for 3 h, the suspension was cooled to room temperature and stirred for 30 min. The crystalline solid was filtered, washed with MTBE (100 mL) and dried under vacuum at room temperature for 12 h to afford (S)-fluoroleucine L-tartaric acid salt (166.0 g, 90% yield), $^1$H NMR (400 MHz, DMSO) δ=7.45 (bs; 5H), 4.13 (q, J=7.1 Hz, 2H), 4.08 (s, 2H), 3.86(t, J=6.6 Hz, 1H) 2.13-1.96(m, 2H), 1.38(d, J=21.6, 3H), 1.36 (d, J=21.7 Hz, 3H), 1.21(t, J=7.1, 3H)

EXAMPLE 6

Preparation of (S)-fluoroleucine D-BOC Proline Salt

A solution of the racemic fluoroleucine (100 g, 0.56 mol) in isopropyl acetate (500 mL) was treated with N-Boc-D-proline (97.1 g, 0.44 mol) in isopropyl acetate (300 mL) while maintaining the temperature at 25-30° C. The mixture was seeded with crystalline (S)-fluoroleucine N-Boc-D-proline salt (1 gram) and continued the stirring for 4h followed by addition of 5-nitrosalicylaldehyde (1.88 g, 0.012 mol). The resulting crystalline slurry was stirred for an additional 12h. The crystalline salt was filtered, washed with isopropyl acetate, and dried under vacuum to obtain (S)-fluoroleucine N-Boc-D-proline salt (150 g, 68%). Chemical purity: >99.5% and Chiral purity: >99.4%, $^1$H NMR (400 MHz, DMSO) δ=5.4 (br s, 2H), 4.08 (q, J=7.0 Hz, 2H), 4.05(t, J=5.1 Hz, 1H), 3.44(t, J=6.5Hz, 1H), 3.37-3.25(m, 2H), 2.23-2.08 (m, 1H), 2.01 (ddd, J=17.7 Hz, 14.2 Hz, 6.2 Hz, 1H), 1.89-1.68 (m, 4H), 1.39-1.34 (om, 12H), 1.33 (d, J=21.8 Hz, 3H), 1.19(t, 7.1 Hz, 3H)

What is claimed is:

1. A processes for preparing a compound of formula IA:

IA.

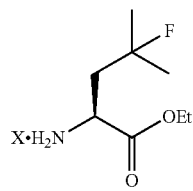

comprising the steps of:
a. alkylating an imine carboxylate of formula IIA with methallyl halide to form a substituted imine of formula IIIA;

IIA.

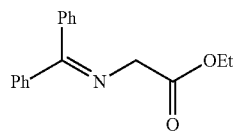

IIIA.

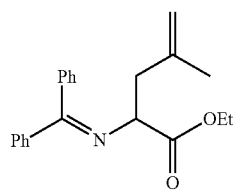

b. deprotecting the substituted imine of formula IIIA with an acid to yield an amine of formula IVA;

IVA.

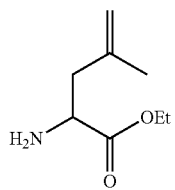

c. resolving the amine of formula IVA with a chiral protic acid selected from the group consisting of D-(+)-camphor-10-sulfonic acid, D-BOC-proline, di-p-tolyl-D-tartaric acid, N-acetyl-D-phenyl alanine and mixtures thereof, in the presence of 5-nitrosalicylaldehyde;
d. fluorinating the resolved amine to yield the compound of formula IA;
wherein X is $H_2SO_4$, L-tartaric acid, D-BOC proline, L-(−)-10-camphorsulfonic acid or N-acetyl-D-phenyl alanine.

2. The process of claim 1, wherein step a. is performed in the presence of a strong base.

3. The process of claim 2, wherein the strong base is selected from the group consisting of potassium t-butoxide, lithium t-butoxide, sodium t-butoxide, LDA, sodium hydride, n-BuLi, sec-BuLi, t-BuLi, LiHMDS, NaHMDS, KHMDS, LiTMP and mixtures thereof.

4. The process of claim 1, wherein step a. is performed in the presence of a polar aprotic solvent.

5. The process of claim 1, wherein the acid is selected from the group consisting of hydrochloric acid, triflic acid, sulfuric acid, p-toluenesulfonic acid, naphthalene disilfonic acid, trifluoroacetic acid and mixtures thereof.

6. The process of claim 1, wherein step d. is performed with a fluorinating agent selected from the group consisting of Olah's reagent, HF-pyridine, HF-triethylamine, HF-Urea, HF-melamine, HF and mixtures thereof.

7. The process of claim 6 wherein the fluorinating agent is Olah's reagent.

8. The process of claim 1, wherein the chiral protic acid is D-(+)-camphor-10-sulfonic acid.

9. A compound of formula IA.

IA.

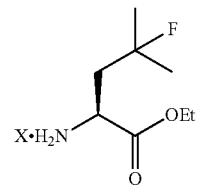

wherein X is L-Tartaric acid, D-BOC proline, L-(−)-10-camphorsulfonic acid or N-acetyl-D-phenyl alanine.

10. A compound of formula

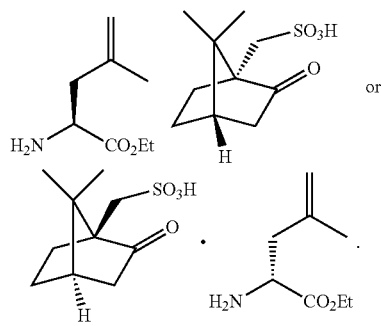

* * * * *